(12) United States Patent
Hattori et al.

(10) Patent No.: US 6,762,312 B1
(45) Date of Patent: Jul. 13, 2004

(54) PROCESS FOR PURIFICATION OF PHYTOSTEROL FROM FATTY ACIDS AND THEIR ESTERS

(75) Inventors: Yasuyuki Hattori, Wakayama (JP); Jun Kono, Wakayama (JP); Masamitsu Horio, Wakayama (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 10/129,329

(22) PCT Filed: Nov. 2, 2000

(86) PCT No.: PCT/JP00/07753

§ 371 (c)(1),
(2), (4) Date: May 3, 2002

(87) PCT Pub. No.: WO01/32682

PCT Pub. Date: May 10, 2001

(30) Foreign Application Priority Data

Nov. 4, 1999 (JP) .......................... 11-313619
Nov. 4, 1999 (JP) .......................... 11-313620

(51) Int. Cl.$^7$ ................................. C07J 9/00
(52) U.S. Cl. ...................................... 552/545
(58) Field of Search .......................... 557/545

(56) References Cited

U.S. PATENT DOCUMENTS

| | | | | |
|---|---|---|---|---|
| 2,866,797 A | * | 12/1958 | Berry et al. | ........... 260/397.25 |
| 3,691,211 A | | 9/1972 | Julian | |
| 5,424,457 A | * | 6/1995 | Sumner et al. | ............. 552/545 |
| 5,487,817 A | | 1/1996 | Fizet | |
| 5,763,353 A | | 6/1998 | Kadono et al. | |
| 5,817,892 A | | 10/1998 | Tamura et al. | |
| 6,383,970 B1 | | 5/2002 | Mimura et al. | |
| 6,407,269 B2 | | 6/2002 | Kaita et al. | |

FOREIGN PATENT DOCUMENTS

| | | |
|---|---|---|
| GB | 895 145 | 5/1962 |
| GB | 895145 | * 5/1962 |
| GB | 1 008 767 | 11/1965 |
| JP | 60 215699 | 10/1985 |
| JP | 61 050996 | 3/1986 |
| WO | 00 61603 | 10/2000 |

* cited by examiner

*Primary Examiner*—Barbara P. Badio
(74) *Attorney, Agent, or Firm*—Oblon, Spivak, McClelland, Maier & Neustadt, P.C.

(57) ABSTRACT

The present invention provides a process for producing a highly pure phytosterol, at high yield in particular, by an easy treatment from a crude fatty acid ester derived from a vegetable fat and/or oil. That is, the present invention provides a process for producing phytosterol, which comprises (A) bringing a crude fatty acid product derived from a vegetable fat and/or oil including phytosterol into contact with a mixed solvent of an organic solvent and water to crystallize the phytosterol and separating the crystals from the mixed solvent; or (B) mixing a crude fatty acid ester derived from a vegetable fat and/or oil including the phytosterol and a fatty acid ester with a lower alcohol, allowing the mixture to stand at a temperature of 1 to 40° C. to precipitate crystals including the fatty acid ester and separating the crystals to take the lower alcohol solution including the phytosterol.

12 Claims, No Drawings

PROCESS FOR PURIFICATION OF PHYTOSTEROL FROM FATTY ACIDS AND THEIR ESTERS

This application is a 371 of PCT/JP00/07753 filed Nov. 02, 2000.

TECHNICAL FIELD

The present invention relates to a process for producing a phytosterol (or plant sterol) from a crude fatty acid ester derived from a vegetable (or plant) fat and/or oil.

BACKGROUND ART

Phytosterols are not only used in clinical administration etc. expected to have an effect of reducing cholesterols in blood but also utilized generally as a raw or starting material for pharmaceutical agents as substitutes for cholesterols or as emulsifiers or emulsion-stabilizers in cosmetics and foods.

As the process for producing phytosterols, a method in which sterols contained in vegetable oils such as a soybean oil, a rapeseed oil, a rice bran oil, a palm oil, a palm kernel oil and a coconut oil are extracted and purified from a deodorized concentrate etc. is practically used. There is known the extracting method which comprises adding a lower alcohol to a deodorized distillate of fats and oils to esterify with an acid catalyst, then washing with water to remove the catalyst, transesterifying by adding an additional lower alcohol and alkali catalyst, calmly laying overnight the resultant solution after the reaction to precipitate crystals, separating the crystals by the filtration, washing with a small amount of hexane to further re-crystallize (JP-B 52-8309).

In this method, however, it is necessary to repeatedly re-crystallize in order to obtain highly pure sterols. Then, it is difficult to more easily obtain highly pure phytosterols.

DISCLOSURE OF INVENTION

The object of the present invention is to provide a process for producing a highly pure phytosterol, at a high yield in particular, by a simple and easy treatment from a crude fatty acid ester derived from a vegetable fat and/or oil.

The invention a process for producing phytosterol, which comprises (A) bringing a crude fatty acid product derived from a vegetable fat and/or oil including phytosterol into contact with a mixed solvent (or solvent mixture) of an organic solvent and water to crystallize the phytosterol and separating the crystals from the mixed solvent; or (B) mixing a crude fatty acid ester derived from a vegetable fat and/or oil including the phytosterol and a fatty acid ester with a lower alcohol, allowing the mixture to stand at a temperature of 1 to 40° C. to precipitate crystals including the fatty acid ester and separating the crystals to take the lower alcohol solution including the phytosterol.

In the method (A), part or all of the treated phytosterol is crystallized. The invention process can be obtained by either the method (step) (A) or (B). Alternatively (A) and (B) may be used in combination with each other.

The present invention provides preferably the above-mentioned process which comprises Steps of (A) and which further comprises allowing a mixture of the crude fatty acid ester with a lower alcohol to stand at a temperature of 1 to 40° C. in order to precipitate crystals including the fatty acid ester.

In the above shown method (A), phytosterol existing in crude fatty acid esters of vegetable fats and/or oils can be concentrated by crystallizing the phytosterol in a solvent mixture of an organic solvent and water. A concentrated phytosterol-including product can be obtained this way.

In the method (B), phytosterol existing in crude fatty acid esters of vegetable fats and/or oils can be concentrated by crystallizing the fatty acid esters in a lower alcohol at a temperature of 1 to 40° C., separating the crystals out and taking the lower alcohol solution including phytosterol. The lower alcohol solution may include remaining fatty acid esters in addition to concentrated phytosterol. A concentrated phytosterol product can be obtained this way.

The invention provides a process for preparing a concentrated phytosterol product, comprising the above shown (A) or (B). (A) and (B) may be continuously repeated to obtained a very concentrated product of phytosterol. (A) and (B) may be used in combination with each other.

The starting material for (A) or (B) may be a natural source of fats and/or oils including phytosterol. It includes phytosterol, fatty acid esters of phytosterol and other fatty acid esters. Alternatively the natural source may be processed in advance to (A) or (B), for example, by treating fatty acid esters by saponification. The saponification may be effected with an alkali and a mixed solvent of a lower alcohol and water. The product of the invention may be saponified this way to obtain a more concentrated phytosterol product.

MODES FOR CARRYING OUT THE INVENTION

The phytosterols in the present invention refer to sterols, contained in vegetable fats and oils, such as sitosterol, stigmasterol, campesterol and brassicasterol.

The vegetable fats and oils used here may be one member of a soybean oil, a rapeseed oil, a rice bran oil, a palm oil, a palm kernel oil and a coconut oil or a mixture of two or more members selected therefrom. Among them, a palm kernel oil, a coconut oil or a palm oil is preferable.

As the crude fatty acid ester derived from vegetable fats and oils in the present invention, there may be preferably used a mixture of various compounds including mainly esters of higher fatty acids with lower alcohols such as esters of $C_{6-28}$ fatty acids with lower alcohols in particular. The composition thereof cannot be specified because the composition is varied depending on the vegetable fats and oils used as the raw material but the composition may also contain monoglycerides, diglycerides, triglycerides, glycerol etc. That is, the crude fatty acid ester is not particularly limited so far as it contains fatty acid esters and phytosterols. For example, there can also be used a crude fatty acid ester obtained by esterifying the above-mentioned deodorized distillate of a vegetable fat and/or oil and then, if necessary, transesterifying with a lower alcohol such as methanol or a raw material obtained by further distilling the said fatty acid ester product according to the technique described in JP-A 8-500598 and increasing the concentration of the phytosterols by distilling a part of the fatty acid ester product formed by the transesterification reaction.

Alternatively, the above-described vegetable fat and/or oil is esterified and then transesterified with a lower alcohol such as methanol, and the fatty ester product thus obtained is distilled to remove distillates, whereby the concentration of the phytosterols can be increased. The raw material concentrated in this manner can also be used. This concentrate contains not only the phytosterols and fatty ester acids but also unreacted monoglycerides, diglycerides and triglycerides having not reacted in the previous transesterification reaction. There can also be used a crude fatty acid ester obtained by further transesterifying the said concentrate.

In general, these raw materials often contain not less than 20% by weight of the esters of the $C_{6-28}$ fatty acids with the lower alcohols. In the present invention, fatty acid esters at such concentrations are also preferably used.

As the fatty acid in the present invention, there can be utilized any one selected from a member and a mixture of two or more members of linear or branched saturated or unsaturated ones. The lower alcohols include $C_{1-4}$ alcohols such as methanol, ethanol, isopropanol, n-propanol and a linear or branched butanol. As the lower alcohol, there can be used a member or a mixture of two or more members thereof. Among them, methanol, ethanol or a mixture thereof is preferable and a methanol-containing member is particularly preferable.

Although the content of the phytosterols in the crude fatty acid ester used in the present invention is not particularly limited, the content is preferably not less than 1% by weight (as compared with the mixture thereof excluding lower alcohols such as methanol) and, in order to exhibit an advantageous effect of the present invention, more preferably 3 to 40% by weight.

In Step A in the present invention, the crude fatty acid ester described above are brought into contact with a mixed solvent comprising an organic solvent and water to crystallize phytosterols. As the organic solvent, there is preferably used one or more solvents having a relative dielectric constant ($\epsilon_r$) of not less than 17 at 25° C. For available easiness; a member or a mixture of two or more members selected from methanol, ethanol and acetone is more preferable and a methanol-containing member is particularly preferable.

The relative dielectric constant of the organic solvent in the present invention referred to the value shown in "Chemical Index Basic-compilation (Kagaku Binran Kisohen)" $4^{th}$ edition published by Maruzen Co., Ltd. or "Solvent (Youzai) Handbook" published by Kodansha.

Although the amount of the organic solvent in the mixed solvent used in Step A is not particularly limited, the amount is preferably from 20 to 300% by weight as compared with the crude fatty acid ester. The amount of water in the mixed solvent comprising the organic solvent and water is preferably larger for improving a recoverable ratio of the phytosterols, but a too large amount of water is not economical because of a longer time for separating the crystals from the solution. Accordingly, the amount of water is preferably not less than 1% by weight and more preferably 5 to 150% by weight as compared with the organic solvent.

The crystallization in Step A is preferably carried out by adding water to the mixture of the crude fatty acid ester and the organic solvent. If the crystallization temperature is high, the amount of the precipitated crystals is insufficient to lower the recoverable ratio of the phytosterols, so that the temperature is preferably from 0 to 40° C. and more preferably from 1 to 20° C. The precipitated crystals are separated from the system (or composition) by publicly known techniques such as filtration, centrifugation and decantation.

This method of the crystallization and separation may comprise adding water, then separating into phases in order to separate a lower phase comprising water/organic solvent, extracting and removing the lower phase, and then separating crystals by allowing an upper phase to stand at a temperature in the range of 0 to 40° C. or may comprise allowing the solution to stand at a temperature in the range of 0 to 40° C., then separating into phases, extracting the lower phase, and then separating crystals from the upper phase. In the method of the crystallization and separation, the solution is separated by adding water to separate into phases, a phase of water/organic solvent as a lower phase is removed by extracting it, and an upper phase is allowed to stand (or kept) at a temperature in the range of 0 to 40° C., whereby the crystals may be separated. Alternatively, the solution is kept at a temperature in the range of 0 to 40° C. and then separated into phases, then a lower phase is extracted, and the crystals may be separated from an upper phase. In any method, the crystals to be precipitated are present in an oil phase, and the solution may be operated to crystallization and separation as it is or may be operated to crystallization and separation after the solution is separated into phases to remove the lower phase. The temperature for separating into phases is not particularly limited, but it is preferably from 0 to 100° C. and more preferably from 0 to 64° C. By these operations, the recoverable ratio of the phytosterols can be significantly improved.

In the present invention, an already known solvent-purifying method i.e. re-crystallization method is applied if necessary to the crystallized precipitation after Step A is finished. The solvent used in this step is mainly an organic solvent such as methanol, but a mixed solvent of an organic solvent and water may also be used. Such an already known re-crystallization step may also be carried out before Step A. That is, if the already known re-crystallization step is used in combination with Step A, the order thereof is not particularly limited.

In the present invention, Step B can be combined before or after Step A or the combined steps of Step A with the already known re-crystallization step. By the combination with Step B, highly pure phytosterols can be extracted at a high yield.

In Step B, the mixture of the crude fatty acid ester and the lower alcohol is regulated such that the amount of the lower alcohol is preferably not less than 2% by weight and more preferably 20 to 300% by weight as compared with the crude fatty acid ester. In this case, a lower alcohol may be additionally (or further) added; however, if the lower alcohol in the esterification step or in the transesterification step of a former step or Step A still remains in the reaction system in the desired amount as compared with the crude fatty acid ester, further addition of the lower alcohol is not required. In short, the presence of the lower alcohol is required and the means therefor is not inquired. The lower alcohol used here includes a $C_{1-4}$ alcohol described above and is preferably methanol, ethanol or a mixture thereof and is particularly preferably a methanol-containing member.

Next, the mixture which comprises the crude fatty acid ester and the lower alcohol and which is regulated as described above is allowed to stand at 1 to 40° C. to precipitate crystals. The crystals thus precipitated comprise the esters of the $C_{6-28}$ fatty acids with the lower alcohol as the main component. These crystals contain little phytosterols. That is, the phytosterols are present as solution components.

The crystallization temperature kept in Step B is very important. Esters of the $C_{6-28}$ fatty acids with the lower alcohol begin to be precipitated as crystals at 50° C. or less. When the temperature for precipitation by crystallizing is high, the amount of precipitation is not sufficient. Namely, there becomes small a contribution in order to improve the purity of the phytosterols. Then, there is lowered the purity of the phytosterols after Step A or the re-crystallization step which is subsequently carried out to the solution from which the crystals have been separated. On the other hand, when the temperature for cooling is too low, the phytosterols are intermixed in the precipitated crystals to lower the recoverable ratio of the phytosterols. Accordingly, the crystallization temperature is controlled in the range of 1 to 40° C. and preferably 3 to 20° C. Further, the time during which the solution is kept at 1 to 40° C. is preferably 0.1 to 2 hours.

Step A in the present invention is carried out after the fatty acid esters in the crude fatty acid ester for use are removed to the utmost, whereby more highly pure phytosterols can be obtained. Accordingly, Step A is most preferably carried out to a filtrate after Step B is carried out.

In Step B of the present invention, further, the precipitated crystals are separated by a publicly known technique as above-mentioned in Step A, whereby the purity of phytosterols after a crystallizing and precipitating treatment being carried out to a rest solution can be significantly improved. That is, an already known solvent-purifying method i.e. crystallizing and precipitating method is applied to the solution from which the precipitated crystals were separated. The solvent used in this step is not particularly limited. For example, methanol, methyl ethyl ketone, ethanol or the like can be used and methanol is particularly preferable.

According to the process of the present invention, highly pure phytosterols can be produced easily and efficiently from a crude fatty acid ester. Further, according thereto, crystals of fatty acid esters can be precipitated highly selectively from the crude fatty acid ester to separate and remove the crystals from the solution containing the phytosterols. Thus, the phytosterols having the significantly improved purity can be obtained without adversely affecting the yield after the crystalline precipitation.

EXAMPLES

The term "%" in Examples is "% by weight" unless otherwise specified.

Example 1

5,000 g of a raw fatty acid methyl ester product derived from a palm kernel oil were distilled to obtain 4,900 g of a distillate and 100 g of a residue. To the residue were added 100 g of methanol (with a relative dielectric constant ($\epsilon_r$) of 32.6 at 25° C.) and 1.0 g of potassium hydroxide. Then, a transesterification reaction was carried out for 2 hours under a condition that the methanol was refluxed. An obtained crude fatty acid methyl ester product contained 68% of methyl esters of $C_{6-28}$ fatty acids and 5.7% of phytosterols (wherein any thereof is a ratio as compared with an oil matter excluding the methanol). The methanol having unreacted remained in an amount of 90% as compared with the crude fatty acid methyl ester product as the oil matter.

Water in an amount of 5.5% as compared with the remaining methanol was added to the solution after the reaction, the solution was kept at a temperature of 5° C., and a crystallizing operation was carried out. The precipitated crystals were recovered at a temperature of 5° C. by using a vacuum filter. 100 g of methanol was further added to the crystals and then they were dissolved again at 60° C. Subsequently, the solution was kept at a temperature of 5° C. and a re-crystallizing operation was carried out to obtain crystals at 5° C. by a filtration under reduced pressure. The obtained crystals were dried in air at 110° C. for 12 hours. The recoverable ratio and purity of the obtained phytosterols are shown in Table 1.

Example 2

An extraction was carried out in the same manner as in Example 1 except that the added amount of water was 55% as compared with the remaining methanol. The recoverable ratio and purity of the obtained phytosterols are shown in Table 1.

Example 3

An extraction was carried out in the same manner as in Example 1 except that the added amount of water was 110% as compared with the remaining methanol. The recoverable ratio and purity of the obtained phytosterols are shown in Table 1.

Comparative Example 1

An extraction was carried out in the same manner as in Example 1 except that water was not added. The recoverable ratio and purity of the obtained phytosterols are shown in Table 1.

Example 4

The same solution after the reaction as in Example 1 was kept at 10° C. for 0.5 hour to precipitate crystals and the crystals were separated and removed by the filtration (at 10° C. of the filtration temperature). The amount of the crystals thus removed was 3.0 g after drying at 110° C. for 12 hours. The crystals contained 95% of methyl esters of $C_{6-28}$ fatty acids but the phytosterols were hardly contained therein.

Water in an amount of 55% as compared with the remaining methanol was added to the filtrate obtained by the filtration, the solution was kept at a temperature of 5° C., and a crystallizing operation was carried out. The precipitated crystals were recovered at a temperature of 5° C. by using a vacuum filter. 100 g of methanol was further added to the crystals and then they were dissolved again at 60° C. Subsequently, the solution was kept at a temperature of 5° C. and a re-crystallizing operation was carried out to obtain crystals at 5° C. at by the filtration under reduced pressure. The obtained crystals were dried in air at 110° C. for 12 hours. The recoverable ratio and purity of the obtained phytosterols are shown in Table 1.

TABLE 1

| | Added amount of water (%) (as compared with methanol *) | Presence or absence of Step B | Recoverable ratio of phytosterols (%) | Purity of phytosterols (%) |
| --- | --- | --- | --- | --- |
| Example 1 | 5.5 | Absence | 35 | 52 |
| Example 2 | 55 | Absence | 69 | 66 |
| Example 3 | 110 | Absence | 68 | 61 |
| Comparative Example 1 | 0 | Absence | 3 | 12 |
| Example 4 | 55 | Presence | 65 | 65 |

*: [Weight of water]*100/[weight of methanol]

Example 5

5,000 g of a raw fatty acid methyl ester product derived from a palm kernel oil were distilled to obtain 4,900 g of a distillate and 100 g of a residue. To the residue were added 100 g of ethanol (with a relative dielectric constant ($\epsilon_r$) of 24.55 at 25° C.) and 1.0 g of potassium hydroxide. Then, a transesterification reaction was carried out for 2 hours under a condition that the ethanol was refluxed. An obtained crude fatty acid ester contained 69% of ethyl esters of $C_{6-28}$ fatty acids and 3.0% of phytosterols (wherein any thereof is a ratio as compared with the oil matter excluding the ethanol). The ethanol having unreacted remained in an amount of 90% as compared with the crude fatty acid ester as the oil matter.

Water in an amount of 55% as compared with the remaining ethanol was added to the solution after the reaction, the solution was kept at a temperature of 5° C., and a crystallizing operation was carried out. The precipitated crystals were recovered at a temperature of 5° C. by using a vacuum filter. The obtained crystals were dried in air at 110° C. for 12 hours. The recoverable ratio and purity of the obtained phytosterols are shown in Table 2.

Comparative Example 2

An extraction was carried out in the same manner as in Example 5 except that water was not added. The recoverable ratio and purity of the obtained phytosterols are shown in Table 2.

TABLE 2

| | Added amount of water (%) (as compared with ethanol *) | Presence or absence of Step B | Recoverable ratio of phytosterols (%) | Purity of phytosterols (%) |
|---|---|---|---|---|
| Example 5 | 55 | Absence | 24 | 26 |
| Comparative Example 2 | 0 | Absence | 0.7 | 1.2 |

*: [Weight of water]*100/[weight of ethanol]

Example 6

A deodorized fraction of a soybean oil was esterified with a sulfuric acid catalyst, neutralized and washed with water to obtain an oil matter. To 100 g of the oil matter were added 100 g of methanol and 1.0 g of potassium hydroxide. Then, a transesterification reaction was carried out for 2 hours under a condition that the methanol was refluxed. The obtained crude fatty acid methyl ester product contained 61% of methyl esters of $C_{6-28}$ fatty acids and 7.0% of phytosterols (wherein any thereof is a ratio as compared with the oil matter excluding the methanol). The methanol having unreacted remained in an amount of 95% as compared with the crude fatty acid methyl ester product as the oil matter.

Water in an amount of 55% as compared with the remaining methanol was added to the solution after the reaction, the solution was kept at a temperature of 5° C., and a crystallizing operation was carried out. The precipitated crystals were dried in air at 110° C. for 12 hours. The recoverable ratio and purity of the obtained phytosterols are shown in Table 3.

Comparative Example 3

An extraction was carried out in the same manner as in Example 6 except that water was not added. The recoverable ratio and purity of the obtained phytosterols are shown in Table 3.

TABLE 3

| | Added amount of water (%) (as compared with methanol *) | Presence or absence of Step B | Recoverable ratio of phytosterols (%) | Purity of phytosterols (%) |
|---|---|---|---|---|
| Example 6 | 55 | Absence | 84 | 62 |
| Comparative Example 3 | 0 | Absence | 51 | 48 |

*: [Weight of water]*100/[weight of methanol]

Example 7

There was used the crude fatty acid methyl ester product obtained in Example 1.

Then, a filtrate obtained by the filtration was neutralized in the range of pH 5 to 7 by adding an aqueous hydrochloric acid (or an aqueous solution of hydrogen chloride). Thereafter, the solution was kept at 5° C. to re-precipitate crystals. 100 g of methanol were added to the crystals to re-crystallize at 5° C. The crystals were dried in air at 110° C. for 12 hours. The dried product thus obtained was 1.84 g and the purity of the phytosterols by a gas chromatography (with Column: ULTRA1 provided by Hewlett-Packard) was 82% (and the recoverable ratio of the phytosterols as compared with the raw material was 27%).

Comparative Example 4

The methanol-containing crude fatty acid methyl ester product after the transesterification in Example 7 was neutralized in the range of pH 5 to 7 with an aqueous hydrochloric acid as it is without crystallizing a precipitation at 10° C. and filtration as shown in Example 7. Thereafter, the solution was kept at a temperature of 5° C. to precipitate crystals. 100 g of methanol were added to the crystals to re-crystallize at 5° C. The crystals were dried in air at 110° C. for 12 hours. The dried product thus obtained was 3.48 g and the purity of the phytosterols by a gas chromatography was 43% (and the recoverable ratio of the phytosterols as compared with the raw material was 27%).

Comparative Example 5

0.1 g of crystal after drying was obtained in the same manner as in Comparative Example 1 except that the methanol-containing reaction solution after the transesterification in Example 7 was treated at 45° C. The crystal contained 99% of methyl esters of $C_{6-28}$ fatty acids but the phytosterols were hardly contained therein.

The filtrate obtained by the filtration was neutralized in the range of pH 5 to 7 by adding an aqueous hydrochloric acid. Thereafter, the solution was kept at 5° C. to re-precipitate crystals. 100 g of methanol were added to the crystals to re-crystallize at 5° C. The crystals were dried in air at 110° C. for 12 hours. The dried product thus obtained was 3.47 g and the purity of the phytosterols by a gas chromatography was 44% (and the recoverable ratio of the phytosterols as compared with the raw material was 27%).

As can be seen from examples and comparative examples, highly pure phytosterols can be obtained in a constant yield by using the process of the present invention.

What is claimed is:

1. A process for purifying phytosterols, comprising
   esterifying a crude fatty acid extract derived from a vegetable fat and/or oil;
   contacting the esterified extract with a mixed solvent of water and an organic solvent to crystallize the phytosterols, wherein the water is present in an amount of at least 55% by weight of the organic solvent; and
   separating the crystallized phytosterols from the solvent.
2. The process of claim 1, wherein the content of the phytosterol in the crude fatty acid extract is not less than 1% by weight.
3. The process of claim 1, wherein the crude fatty acid ester contains not less than 20% by weight of esters of $C_{6-28}$ fatty acids with lower alcohols.
4. The process of claim 1, wherein the organic solvent has a relative dielectric constant ($\epsilon r$) of not less than 17 at 25° C.

5. The process of claim 1, wherein the organic solvent is methanol.

6. The process of claim 1, wherein the vegetable fat and/or oil is a palm kernel oil, a coconut oil, or a palm oil.

7. A process for purifying phytosterols, comprising
esterifying, in an organic solvent, a crude fatty acid extract derived from a vegetable fat and/or oil;
precipitating the crude fatty acid ester at a temperature of from 1 to 40° C.;
recovering the organic solvent from the fatty acid fatty acid ester precipitate;
adding at least 55% water by weight of the organic solvent to crystallize the phytosterols; and
separating the crystallized phytosterols from the solvent.

8. The process of claim 7, wherein the content of the phytosterol in the crude fatty acid extract is not less than 1% by weight.

9. The process of claim 7, wherein the crude fatty acid ester contains not less than 20% by weight of esters of $C_{6-28}$ fatty acids with lower alcohols.

10. The process of claim 7, wherein the organic solvent has a relative dielectric constant ($\epsilon r$) of not less than 17 at 25° C.

11. The process of claim 7, wherein the organic solvent is methanol.

12. The process of claim 7, wherein the vegetable fat and/or oil is a palm kernel oil, a coconut oil, or a palm oil.

* * * * *